US009245658B2

(12) United States Patent
Desaute (10) Patent No.: US 9,245,658 B2
(45) Date of Patent: Jan. 26, 2016

(54) IMAGING APPARATUS AND METHOD (75) Inventor: Pascal Desaute, Paris (FR)

(73) Assignee: EOS IMAGING, Paris (FR)

(*) Notice: Subject to any disclaimer, the term of this patent is extended or adjusted under 35 U.S.C. 154(b) by 288 days.

(21) Appl. No.: 13/696,428

(22) PCT Filed: May 6, 2010

(86) PCT No.: PCT/IB2010/001806
§ 371 (c)(1),
(2), (4) Date: Nov. 6, 2012

(87) PCT Pub. No.: WO2011/138632
PCT Pub. Date: Nov. 10, 2011

(65) Prior Publication Data
US 2013/0058459 A1  Mar. 7, 2013

(51) Int. Cl.
*G21K 1/04* (2006.01)
*A61B 6/03* (2006.01)
*A61B 6/06* (2006.01)
*A61B 6/00* (2006.01)
*G03B 42/02* (2006.01)
*G03B 42/04* (2006.01)

(52) U.S. Cl.
CPC . *G21K 1/04* (2013.01); *A61B 6/032* (2013.01); *A61B 6/06* (2013.01); *A61B 6/4014* (2013.01); *A61B 6/4441* (2013.01); *A61B 6/545* (2013.01); *G03B 42/02* (2013.01); *G03B 42/025* (2013.01); *G03B 42/04* (2013.01)

(58) Field of Classification Search
CPC ............ A61B 6/03; A61B 6/032; A61B 6/06; A61B 6/44; A61B 6/4429; A61B 6/429; G21K 1/02; G21K 1/025; G21K 1/04

USPC ............ 378/10, 11, 12, 25, 62, 95, 147, 151, 378/156
See application file for complete search history.

(56) References Cited

U.S. PATENT DOCUMENTS

| 4,143,273 | A |   | 3/1979 | Richey et al. |
|---|---|---|---|---|
| 4,200,799 | A |   | 4/1980 | Saito |
| 5,307,396 | A | * | 4/1994 | Tsuchino ...................... 378/146 |
| 5,386,446 | A | * | 1/1995 | Fujimoto et al. ................ 378/20 |
| 5,521,956 | A |   | 5/1996 | Charpak |

(Continued)

FOREIGN PATENT DOCUMENTS

| EP | 0223432 A2 | 5/1987 |
|---|---|---|
| EP | 0678896 A1 | 10/1995 |

(Continued)

OTHER PUBLICATIONS

International Search Report of PCT/IB2010/001806; Jan. 12, 2011; Bataille, Frederic.

(Continued)

*Primary Examiner* — Jack Berman
*Assistant Examiner* — David E Smith
(74) *Attorney, Agent, or Firm* — BCF LLP (57) ABSTRACT

An imaging apparatus has an emission device to emit X-rays and a detection device to detect X-rays. A detector collimator is located between the patient space and the detection device. The emission device and detection device operate while translating along a displacement axis, to take a plurality of acquisitions. The imaging apparatus has a setting device to modify a dimension of a collimator slit.

6 Claims, 6 Drawing Sheets

(56) References Cited

U.S. PATENT DOCUMENTS

| | | | |
|---|---|---|---|
| 5,684,855 A | 11/1997 | Aradate et al. | |
| 5,864,597 A * | 1/1999 | Kobayashi | 378/4 |
| 5,959,302 A | 9/1999 | Charpak | |
| 6,173,033 B1 * | 1/2001 | Klingenbeck-Regn et al. | 378/20 |
| 6,243,438 B1 * | 6/2001 | Nahaliel et al. | 378/19 |
| 6,621,891 B2 * | 9/2003 | Danielsson | 378/150 |
| 2007/0009092 A1 | 1/2007 | Ikeda | |
| 2010/0246752 A1 * | 9/2010 | Heuscher et al. | 378/4 |
| 2012/0027174 A1 * | 2/2012 | Takamura | 378/62 |

FOREIGN PATENT DOCUMENTS

| | | | |
|---|---|---|---|
| EP | 1168249 A1 | 1/2002 | |
| FR | 2749402 A1 | 12/1997 | |
| JP | H08280659 A | 10/1996 | |
| WO | WO 2009004410 A1 * | 1/2009 | |

OTHER PUBLICATIONS

English Abstract of EP1168249 Published Jan. 2, 2002.

English Abstract of FR2749402 retrieved from Espacenet on Sep. 1, 2015.

English Abstract of EP0678896 retrieved from Espacenet on Sep. 1, 2015.

* cited by examiner

IMAGING APPARATUS AND METHOD

FIELD OF THE INVENTION

The instant invention relates to imaging apparatus and methods.

BACKGROUND OF THE INVENTION

In particular, the instant invention is related to an imaging apparatus comprising:
- an emission device adapted to emit X-rays, in an irradiation plane comprising an incidence direction,
- a detection device adapted to detect X-rays,
- a patient space being defined between said emission device and detection device, and adapted to receive a patient to be imaged,
- a detector collimator located between said patient space and said detection device, said detector collimator comprising a X-ray absorbing plate in which a X-ray transparent detector slit is formed,
- a motoring device adapted to cause a relative movement of the emission device, the detection device and the detector collimator relative to the patient, along a displacement axis normal to the irradiation plane,
- wherein said detector slit has at least one dimension, along the displacement axis,
- a control device adapted to cause the emission device and detection device to operate during said movement, so as to take a plurality of acquisitions, each taken along the same incidence direction, and each in a respective one of a plurality of different positions along said displacement axis.

EP-A-1 168 249 already describes such an imaging apparatus, which is very beneficial in that it is operable to take a radiograph of a full segment of the patient (sometimes even the full body).

Due to the usefulness of the apparatus as described above, it is to be applied in an ever-broadening range of applications.

The instant invention has notably for object to facilitate the use of the above apparatus in a wide range of applications.

SUMMARY OF THE INVENTION

To this aim, an imaging apparatus comprises a setting device adapted to modify said dimension of said detector slit.

With these features, it is possible to adapt the features of the imaging apparatus to the patient to be imaged, and/or to the examination to be conducted.

In some embodiments, one might also use one or more of the features defined in the dependent claims.

BRIEF DESCRIPTION OF THE DRAWINGS

Other characteristics and advantages of the invention will readily appear from the following description of three of its embodiments, provided as non-limitative examples, and of the accompanying drawings.

On the drawings.

On the different Figures, the same reference signs designate like or similar elements.

DETAILED DESCRIPTION

Figure 1:
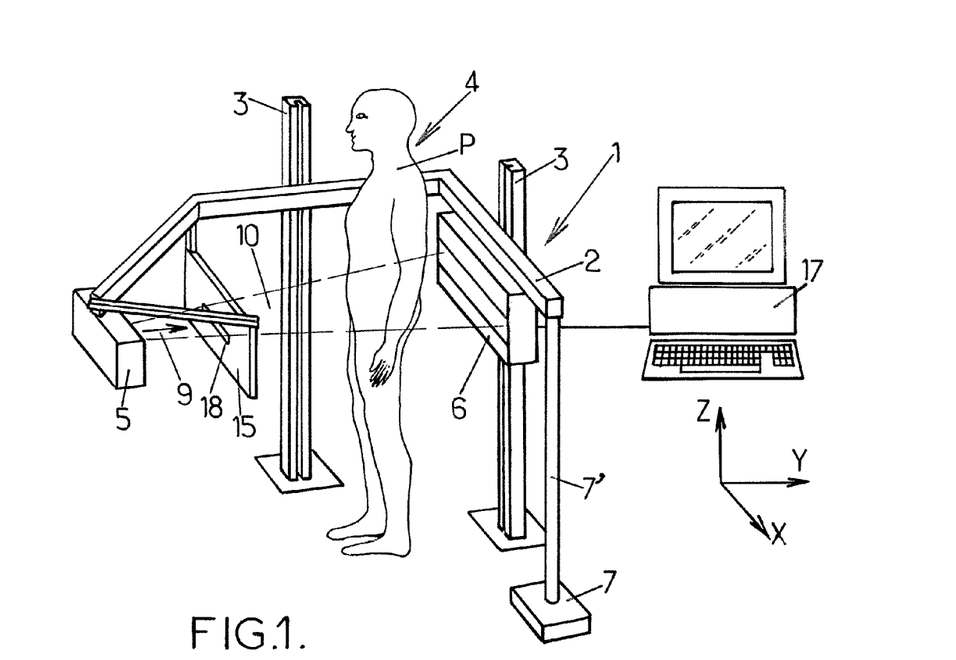
FIG. 1 is a perspective view of an imaging apparatus according to a first embodiment.

FIG. 1 shows an imaging device 1 according to a first embodiment. This device comprises a frame 2 which defines an observation field 4 (patient space) in which a patient can be placed. The mobile frame 2 can be displaced by a motor 7, by way of any suitable kind of movement transfer device 7', along guides 3, in translation along a vertical longitudinal axis Z with respect to the patient space 4.

The mobile frame 2 carries a radiation generator 5 and a detector 6. For example, in the following description, these devices are spaced apart along an incidence direction Y.

These radiation generator and detector can for example be of a type known to the skilled person.

The X and Y directions define the plane normal to the Z direction. With the illustrated orientation of the patient in the apparatus, Y corresponds to the antero-posterior direction of the patient, and X as the remaining horizontal direction (lateral direction of the patient).

A radiation generator 5 comprises an X-ray source which generally emits X-rays in a large solid angle (not shown on the figure). The X-ray source is therefore encased in a X-ray absorbent housing 12 comprising a X-ray transparent window adapted to ensure that, upon operation of the X-ray source, a beam of emitted X-rays 9 is emitted mainly toward the patient P to be imaged.

The detector 6 is arranged facing the corresponding source on the other side of the field 4.

The detector 6 is designed to detect the energy of the X-rays arriving at and passing through an anatomical part of the patient being analyzed. The detector delivers signals corresponding to the transmitted radiation to a computer 17.

The movement of the frame 2 is controlled by logic executed by a computer 17 or other electronic control system. There are many suitable ways to embody logic for the purpose of the invention, which ways will not be described in details here.

The computer 17 can also control operation of the source 5 and/or detector 6.

Since the detector needs to be read out from time to time during the acquisition, the computer 17 can command the reading-out of the detector at a given frequency. This read-out command might be pre-programmed and fixed, and/or might be made in synchronism with the displacement of the frame 2.

The computer 17 can also be provided with recording means (the memory of the computer 17) for recording the signals delivered by the detector.

Figure 2:
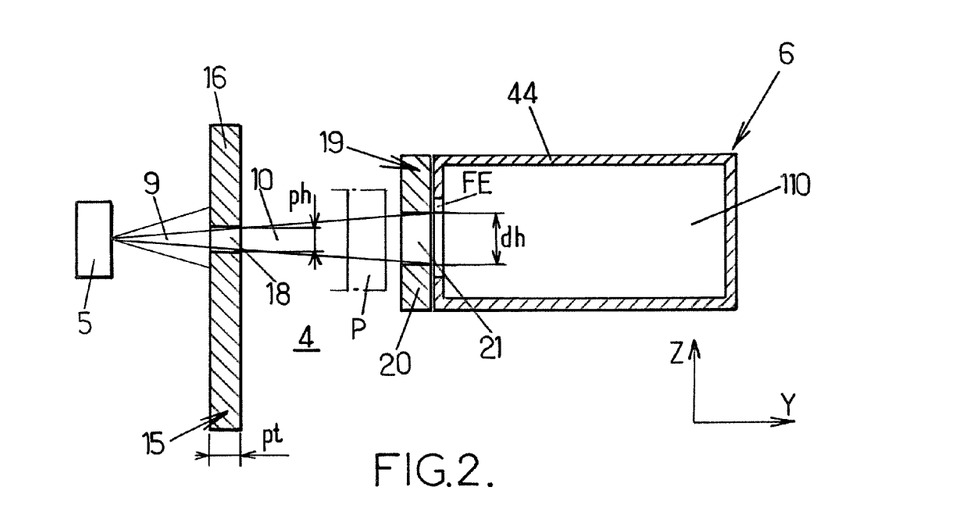
FIG. 2 is a partial lateral view of the apparatus of FIG. 1.

FIG. 2 is a lateral view of the system of FIG. 1 (not to scale). As shown, a patient collimator 15 is disposed downstream of the source (where downstream refers to the propagation of the X-rays from the source), and upstream of the patient space 4. The patient collimator 15 can comprise an X-ray absorbent plate 16 (for example made from a sufficiently thick copper and tungsten alloy or lead) through which a X-ray transparent slit 18 is formed. The patient collimator 15 is designed to intercept the emitted X-rays 9 and to precisely define an X-ray beam 10 which will impact on the patient. The slit 18 forms a diaphragm enabling a planar (slightly divergent) X-ray fan beam to be provided in the X-Y plane (irradiation plane) for irradiation of the part of the subject P being imaged. The slit 18 is defined by its geometry, having one dimension, or height ph which is defined along the direction of scanning, i.e. the Z axis. The slit also has one dimension pw, or width, defined along the lateral dimension of the patient (here, pw is measured along the axis X). To ease the description, the slit will be considered to have a rectangular section in the XZ plane in the rest of the description, although the invention is not limited to rectangular slits. Another dimension of interest for the slit 18 is its thickness pt along the direction of emission of the X-rays (measured along the axis Y). An irradiation plane is defined as substantially a middle plane, defined by the slit 18 and comprising the source, in which the X-rays extend, and comprises an incidence direction (direction source-detector, here Y) and a transverse direction (here X).

A detector collimator 19 is disposed downstream of the patient. The detector collimator 19 can comprise an X-ray absorbent plate 20 (for example made from a sufficiently thick copper and Zinc alloy) through which a X-ray transparent slit 21 is formed. The detector collimator 19 can help to eliminate scattered radiation generated by the object P. The detector collimator is designed to precisely define the angular acceptance of the X-ray beam 10 which will impact on the detector after passing through the patient space. The slit 21 is defined by its geometry, having one dimension dh, or height, measured along a direction parallel to that along which the dimension ph of the patient collimator is measured (here direction Z). This slit also has one dimension dw, or width measured along a direction parallel to that along which the dimension pw of the patient collimator is measured (here direction X). To ease the description, the slit will be considered to have a rectangular section in the XZ plane in the rest of the description, although the invention is not limited to rectangular slits. The detector collimator 19 can be placed over the detector 6, so that the slit 21 is placed in front of a radio-transparent entrance window FE for the detector 6.

According to an embodiment of the invention, the distance between the focal spot of the X-ray source and the plane of the detector collimator is about 1300 mm. The distance between the focal spot of the X-ray source and the patient collimator is about 450 mm. For medical imaging, these dimensions are thought to optimise the size of the patient cabin and the patient's accessibility into the cabin, taking into account the potential image quality regarding the source-detector distance. However, other dimensions are possible such as, for example, for security control applications.

The collimators 15 and 19 are moved together with the associated source and detector, being for example fixed to the frame 2.

As visible on FIG. 2, according to a first embodiment of the invention, the detecting device 6 comprises a gaseous detector 44. Suitable detectors are for example described in FR 2 749 402 or EP 0 678 896 which are hereby incorporated by reference in their entirety for all purposes. The gaseous avalanche detector 44 includes a gas chamber 110 provided with an entrance window FE through which the beam of X-rays to be detected enters the detector 44. The entrance window FE is aligned in parallel with the collimator slits 18 and 21 and allows the X-ray beam to enter the detector 6 with a high level of transmissibility while providing a reliable seal against leakage of the gas from the gas chamber 110 at atmospheric pressure or higher operational pressures. In the gas chamber, the transmitted X-rays interact with the gas to provide a detectable signal indicative of the energy of the X-ray.

The drawing of FIG. 2 is an ideal representation, where the anode of the X-ray source is idealized as a point source, at least along the vertical extension (along direction Z). However, in real life, as shown on FIG. 3, the X-ray source is not punctual, but has a given vertical extension sh. This is firstly due to the fact that the area of the anode emitting X-ray is not a pure point source; this can also be increased, for example, because the anode target 37 of the anode 36 is angled with respect to the direction Y, thus has an extension along the axis Z, and/or for example, when the anode is of the rotating-anode type, due to the wobbling of the anode during its rotation around its rotation axis, or for any other reason depending on the kind of anode technology.

Figure 3:
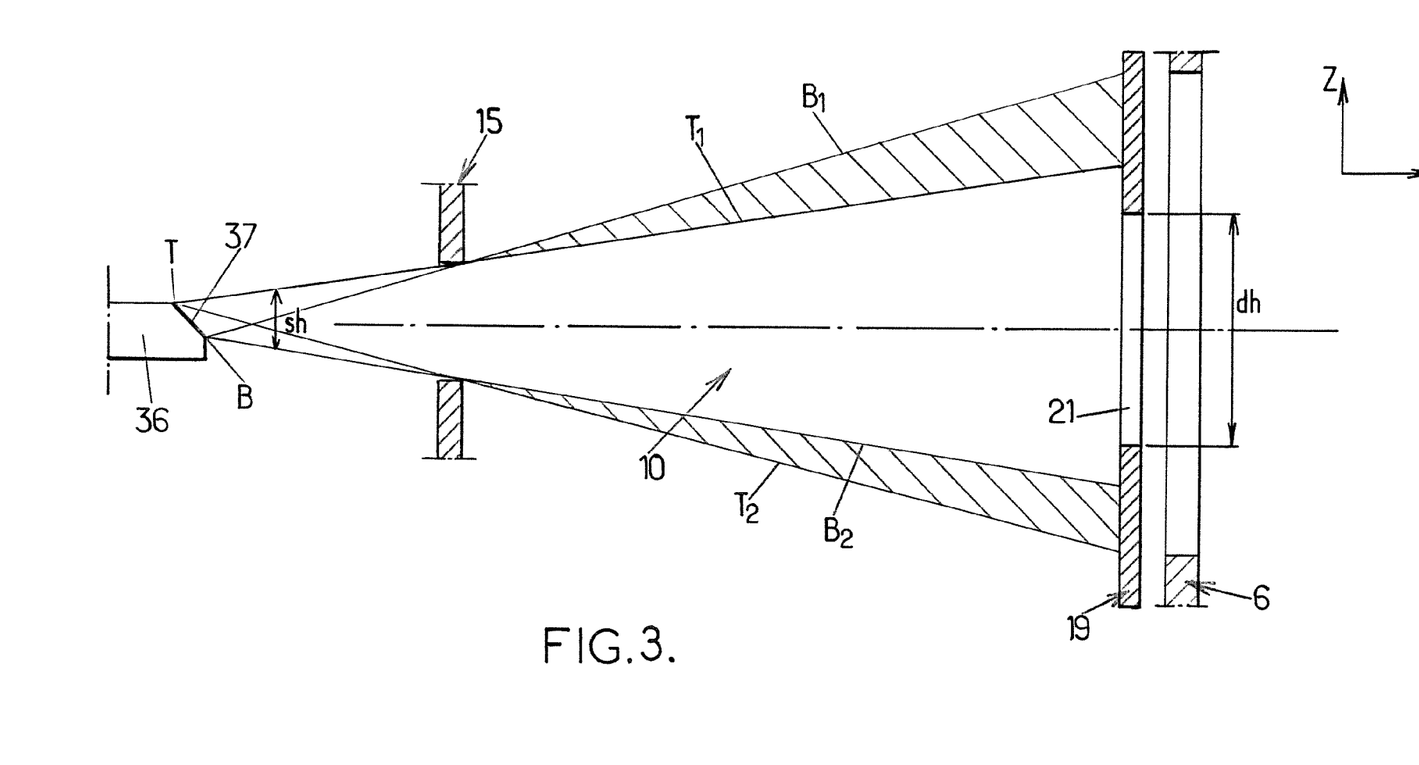
FIG. 3 is an enlarged view of FIG. 2.

Hence, in real life, the emitted X-ray beam, should be considered as a summation of individual elementary X-ray beams emitted by each corresponding elementary point of the anode along the axis Z.

In the first embodiment, as shown, the detector 6 has a single line of detector cells. This means that detector cells are provided all along the direction X. This is for example the case for gaseous detectors such as described above. In such case, the vertical resolution of the X-ray image is directly defined by the dimension dh of the slit 21 of the detector collimator 19.

The X-rays which pass through the patient during examination are defined as the ones passing through the patient collimator 15. Due to the fact that the source has an extension sh along the vertical direction, these X-rays are encompassed within an envelop defined by the X-rays emitted by the top most point T and the bottom most point B of the anode. The envelop of the X-rays which pass through the patient and are emitted by the point T is defined by the lines $T_1$ and $T_2$ on FIG. 3a. Similarly, the envelop of the X-rays passing through the patient and emitted from the point B is defined by the lines $B_1$ and $B_2$ on FIG. 3.

A more detailed description of the detector collimator 19 is given below, by reference to FIG. 4. As shown, a setting device 29 is used to set the dimension of the slit 21 along the axis Z (scanning direction). For example, the setting device 29 comprises a radio-opaque plate 20 of the detector collimator 19, and a radio-opaque flap 30a which is movable with respect to the plate 20, between a maximal opening position and a minimal opening position (on FIG. 4, the flap 30a is shown in an intermediate opening position). The flap 30a might be guided for movement with respect to the plate 20 by any suitable guiding device, such as rails 31 of the plate receiving complementary rails 32 of the flap 30a. A motoring device 33 can be used to displace the flap 30a with respect to the plate 20. Any suitable motoring device can be used such as an electro-mechanical actuator. The motoring device 33 can be operated under control from the computer 17.

For example, the dimension ph of the height of the slit can be set using the flap 30a, and a flap 30b symmetric to the flap 30a with respect to the axis X. The motoring device 33 of the flap 30b can be operated under control from the computer 17, independently or dependently (in particular symmetrically) of the motoring device 33 of the flap 30a.

For example, the dimension (height) of the slit along the scanning direction is settable between about 100 micrometers and 2 millimeters.

Optionally, the dimension pw of the width of the slit can also be set using one or two (as shown) flaps 30c, 30d, operating in a similar way along the direction X, to center the X-ray beam onto the patient.

Figure 4:
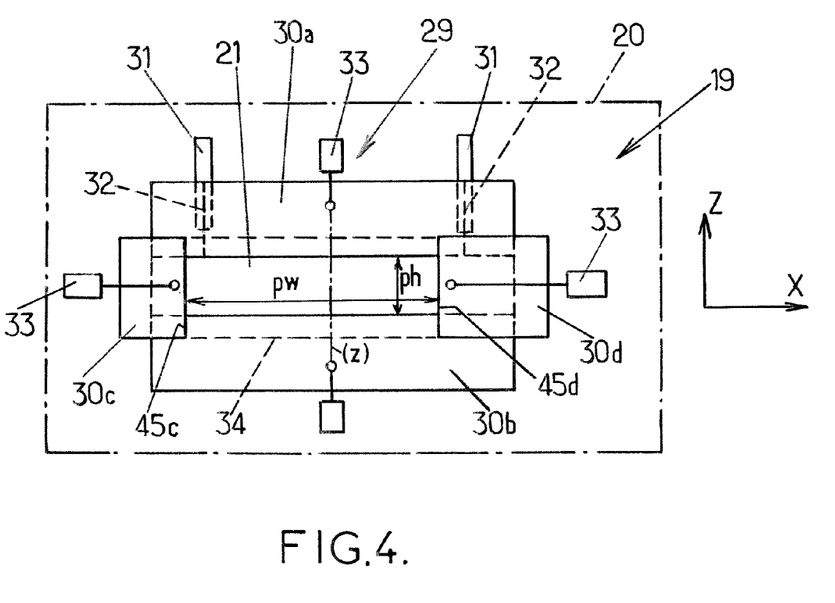
FIG. 4 is a planar partial view of a collimator.

On FIG. 4, the fully opened condition of the slit is shown by the dotted line 34.

The same description could be applied to the patient collimator 15. The dimensions of the slit 18 of the patient collimator 15 will not necessarily be identical to those of the detector collimator 19. One or more dimensions of the slit 18 could be set dependently on a corresponding dimension of the slit 21, or independently therefrom. For example, the dimension (height) of the slit of the patient collimator along the scanning direction is settable between about 100 and 2 millimeters. The other dimension (width) of the slit is settable so as to define a half-angle of the X-ray beam between 0° and 10° from the mid-plane Y-Z of the imager.

The device which has just been described operates as follows.

A patient to be imaged is placed in the patient space 4. Imaging parameters are determined. Such parameters are for example patient-specific and/or specific to the image to be taken and can for example include:

the start and/or stop positions of the frame 2,
the displacement profile (for example speed profile) of the frame 2,
characteristics of the X-ray source 5 (for example voltage and/or intensity profile of the source 5),
characteristics of the slit 21 (and optionally of 18) (for example, their dimensions),
characteristics of the detector 6 (for example its read-out frequency).

Such parameters could be defined by trained medical personal, using the computer 17. Alternately, these parameters could be pre-set as standard values in a database of the microcomputer. Another option is that these parameters could be defined to be patient-specific and/or examination specific. In such case, they may be defined by a computing device of the computer 17 using a database taking for input some patient-specific parameters. In particular, some patient-specific parameters such as weight or some physiological measurements, which do not need to be determined by extremely well-trained medical personal, could be entered as inputs to the database, and some or all of the above imaging parameters determined therefrom.

For example, it is determined to have a full-body image of a patient of average height and weight. The start and stop positions are determined from the height of the patient, and the frame 2 is moved to its start position.

The characteristics of the frame 2, X-ray source 5 and of the detector 6 are set. For example, the frame 2 will move at constant speed, and the detector will be read-out at a given constant frequency.

Further, the dimensions of the slits 18 and 21 are set. For example, these dimensions are set to be constant over the whole displacement of the frame from its start to its stop positions along the axis Z.

The width dw of the slit 18 of the detector collimator is set so that the whole width of the X-ray beam 10 will be detected. The height dh of the slit of the detector collimator will be set for example to provide a given vertical resolution of the image.

Then, the height ph of the slit of the patient collimator will be set, taking into account the height dh of the slit of the detector collimator. For example, it will be set, as shown on FIG. 5a, so that any point of the detector will see the whole vertical extension sh of the source. In other words, it will be set so that the lines $T_1$ and $B_2$ will pass through the edges of the slit 21 of the detector collimator 19. Hence, it is chosen to exclude from the detection X-rays such as the ray Bx as shown on FIG. 5a, since the point MP of the detector which would detect this ray cannot see the whole vertical extension of the anode (the top most region of the anode being masked by the top most region of the collimator 15).

Figure 5A:
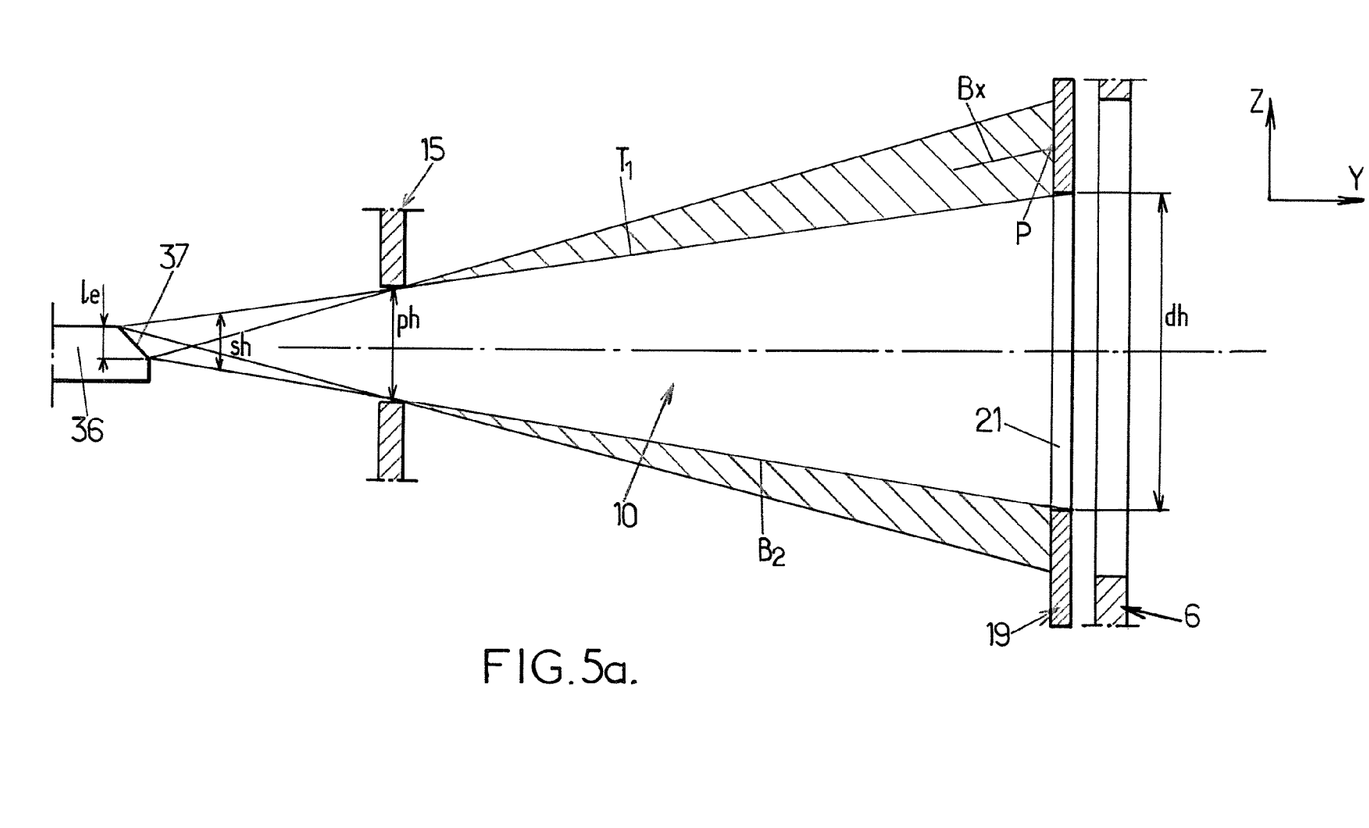
FIGS. 5a and 5b are views corresponding to FIG. 3, in other configurations.

In this embodiment, the image resolution is appropriate, which is suitable for imaging considerations, but the patient is irradiated by rays which are not used for detection, such as ray Bx. Hence, the ratio of the useful signal to the emitted signal is not optimal. "Useful signal" designates the part of emitted signal which is to be useful for the detection, i.e. the signal encompassed between $T_1$ and $B_2$ in this drawing.

Figure 5B:
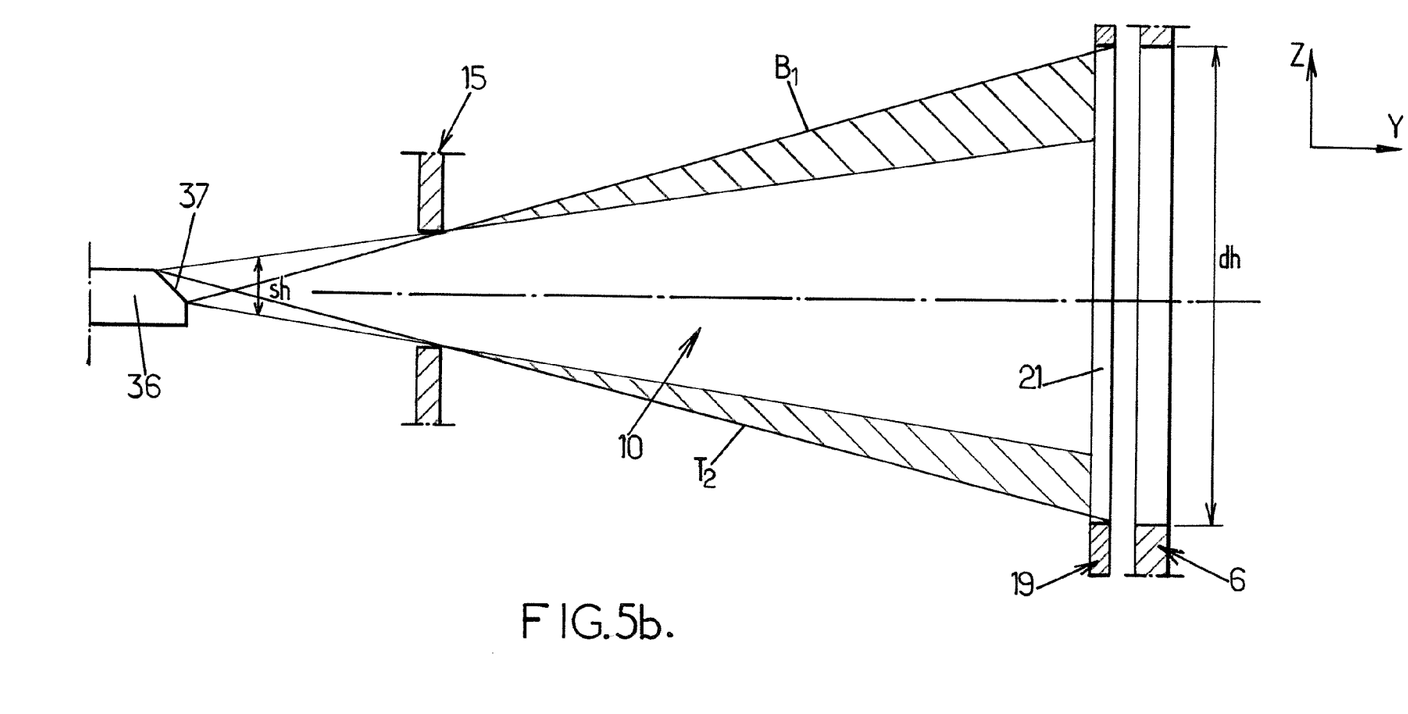

A variant operation is shown on FIG. 5b. For description of FIG. 5b, the opening of the slit of the patient collimator 15 is kept the same as on FIG. 5a. Compared to FIG. 5a, the height dh is increased so that all the X-rays passing through the patient are detected. Stated otherwise, the lines $B_1$ and $T_2$ now pass through the edges of the slit 21 of the detector collimator 19. With this configuration, all the X-rays passing through the patient are used for signal detection. However, the resolution of the image has decreased, since the height dh has increased. It will be noted that the height dh of the detector collimator can be increased for example up to the height of the entrance window FE of the detector 6.

In this embodiment, it is therefore possible to define the compromise which is the best between the image resolution on one side, and the ratio of the useful dose to the emitted dose of the other side, for any specific examination. This compromise can be made for every patient, and/or every medical examination based on the specific practitian or patient requirements.

This determination can be based on one or more of the followings:

patient measurements, such as geometrical and/or physiological measurements,
patient specific requirements,
examination specific requirements,
a preliminary examination of a patient, such as a preliminary X-ray imaging of the patient, preferably at low energy, for example using the same imaging apparatus,
a priori knowledge, such as a database enabling to determine a slit opening based on one or more of the above .
. . .

Figure 6:
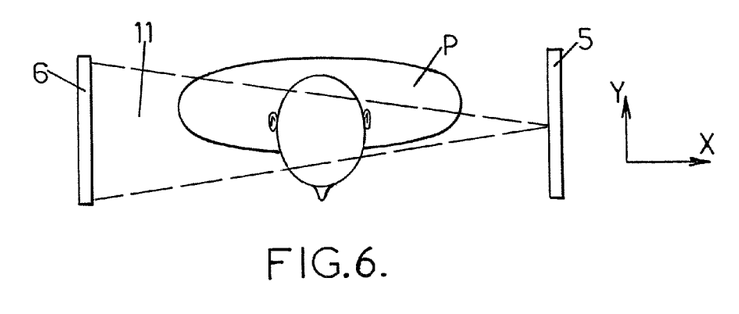
FIGS. 6 and 7 are top views showing a second, respectively third embodiment of the invention.

According to a second embodiment, as shown on FIG. 6, after performing the frontal image, if a lateral image of the patient is to be taken, the frame 2 can be rotated 90° around the axis Z. The stop position of the first scan will be the start position of the second scan.

If the frame 2 and the observation field 4 are movable in rotation with respect to one another about the vertical axis Z, the relative position of the source-detector axis and of the field 4 can be modified by an angle of between 0 and 90 degrees, in a plane normal to the horizontal axis Z. Thus, the radiation-generating means can emit the X-rays in several incidences respective to the patient, and in particular in two orthogonal incidences.

Of course, the vertical dimension of the slits could be modified to take into account the fact that the dimensions (thickness and breadth) of the patient, frontally and laterally, may be different. Regarding the horizontal dimensions, although the dimension u of the slit was symmetrical with respect to the central vertical plane of the imaging apparatus 1, the two flaps 30c and 30d could be modified independently for the lateral imaging, to take into account the size of the belly of the patient P.

Figure 7:
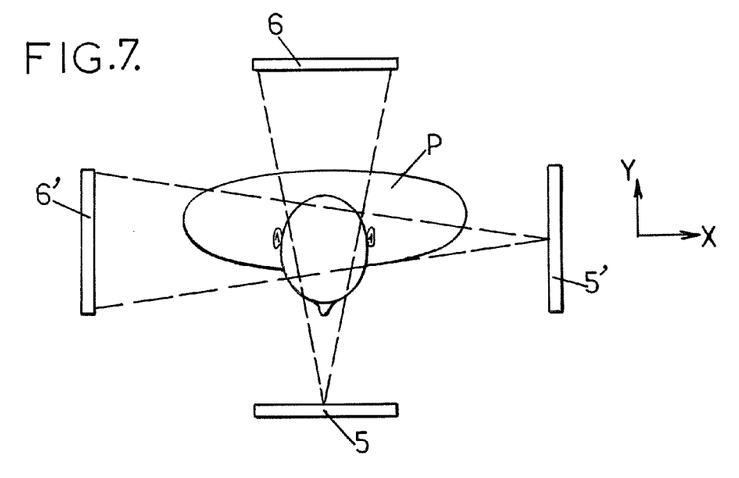

According to a third embodiment, as shown on FIG. 7, further to the antero-posterior imaging which has just been described, a lateral imaging could be performed by a distinct source 5' and detector 6', along a distinct direction of incidence of X-rays. This would for example allow taking the two images simultaneously, thereby limiting the risk of movement of the patient between the two acquisitions. For example, the two sources 5 and 5' and detectors 6 and 6' can be carried by a same frame 2.

The above embodiments are useful for imaging the patient P in a position which is an actual under-load position of the patient, such as standing in particular for orthopaedics applications.

However, according to another embodiment, scanning could be performed horizontally with respect to a lying patient.

In any of the above embodiments, the height dh of the slit 21 of the detector collimator is described to be set constant for a given scan. In a variable embodiment, which could be used in any of the above embodiments, this height could be set to be variable during a given scan. When the patient is scanned from a region A (for example, the head) to a region B (for example, the feet) this height dh could be modified during the scanning, to increase the resolution in areas where increased resolution is deemed necessary, or to improve the ratio of the useful signal to the emitted signal in region of the patient where this is deemed useful. For example, when imaging the spine of an overweight patient, the resolution could be improved in regions where the patient is thin (for example, the cervical vertebrae) and could be decreased where the patient is thick (for example the lumbar vertebrae). The opening strategy of the slit could be totally determined in advance of the imaging. Alternatively, it could be determined dynamically during the scan. In such case, for example, the most recent (i.e. corresponding to the previous line) detection data could be analysed and this analysis could lead to the opening or the closing of the slit for the continuation of the scan. This analysis could for example be based on whether, based on the present detection data, it seems necessary to improve the ratio of the detected signal to the emitted signal or, to the contrary, whether it seems possible to reduce this ratio, thereby improving the resolution.

Figure 8:
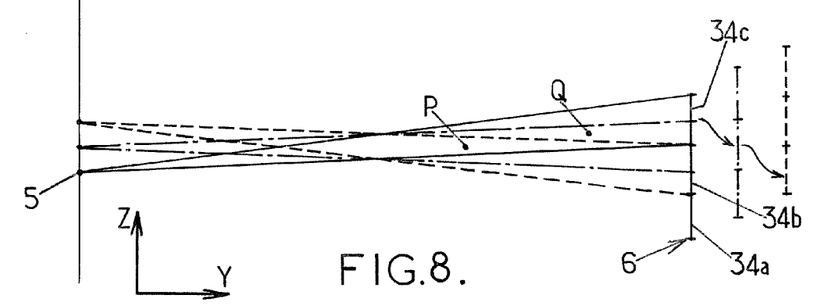
FIG. 8 is a schematic explanation for an imaging apparatus using another detection technology.

According to a variant embodiment, as schematically shown on FIG. 8, one does not necessarily use a gaseous detector. One might also use a solid detector performing time delay integration (TDI). In any of the above embodiments, a gaseous detector could be replaced by a TDI detector. According to this detection method, a detecting cell having a height dh as defined by the slit 21 of the detector collimator 19, for a gaseous detector, will be replaced by a plurality of cells (for example 10 to 100 cells) disposed along the direction Z. Three cells 34a, 34b, 34c are schematically shown on FIG. 8. On FIG. 8, the geometry of the system is shown in straight lines for a first time, in mixed lines for a second time, and in dotted mixed lines for a third time. At the second and third times, the detector is shown offset laterally with respect to the detector at the first time for clarity reasons but, in reality, the detector moves along the axis Z only.

At the first time, the source 5 and detector 6 are in a first position. Each cell 34a, 34b, 34c receives signals corresponding to X-rays transmitted through different regions of the patient. In particular, the cell 34c receives a signal passing through the point P of the patient. The other cells also receive signals, although this is not shown on the figure for clarity purposes.

At the second time, both the source 5 and the detector 6 have moved along the direction Z to a second position. As visible, the cell 34b will now receive a signal corresponding to X-rays transmitted through the point P of the patient. However, in the meanwhile, the signal received in the cell 34c for the first time, has been electronically shifted to the detecting cell 34b. At the third time, it is the cell 34a which will receive the signal passing through the point P of the patient. Between the second and the third time, the signal has been electronically shifted from the cell 34b to the cell 34a. Hence, by carefully synchronizing the displacement of the frame with the cell-shifting frequency, signals corresponding to X-rays transmitted through the point P of the patient accumulate throughout the time during which the point P is within the emitted X-ray beam. The last cell is read-out to the computer 17.

For this detection technology, the trade-off (compromise) to be made by the use of collimators with slits with settable opening along the scanning direction is that of the field of the depth of the image to the signal. If the slit is opened more, the signal will be increased. Indeed, it will be understood from the above description that, if the detector slit defines an opening corresponding only to two cells 34ac and 34b, less signal will be detected for the point P, compared to the case where the slit is sufficiently open, for the three cells 34c, 34b and 34a to receive signal for the point P during imaging.

However, with this technology, the more the detector slit is opened, the lower the field of depth is. As can be seen on FIG. 8, the point Q of the patient, which is located behind the point P, will be seen at the first time by the cell 34c, and at the second time by the cell 34b, but not at the third time by the cell 34a. Thus, when the detector slit is opened to correspond to the two cells 34c and 34b, the field of depth of the image will encompass at least points P and Q. When it is opened to correspond to all three cells, information related to point Q will be blurred. Of course, this phenomenon given for three cells for the sake of clarity, is magnified when thousands of cells come into play.

In variants of any of the above embodiments, the X-ray source 5 and the detector 6 can be fixed while the subject P is moved with an appropriate displacement to provide an image.

For any of the above embodiments, the computer 17 might have, in its memory, a three-dimensional generic model of some of the imaged objects. This generic model corresponds, for example, to a specific specimen or to an average form of the object in question, which generic model, in the latter case, is produced in advance by statistical methods and by analyzing a large number of similar objects. The generic model can be adapted to the patient-specific images to produce a three-dimensional image of the patient's structure.

The invention claimed is:
1. An imaging apparatus comprising:
an emission device adapted to emit X-rays, in an irradiation plane comprising an incidence direction,
a detection device adapted to detect X-rays,
a patient space being defined between said emission device and detection device, and adapted to receive a patient to be imaged,
a detector collimator located between said patient space and said detection device, said detector collimator comprising a X-ray absorbing plate in which a X-ray transparent detector slit is formed,
a motoring device adapted to cause a relative movement of the emission device, the detection device and the detector collimator relative to the patient, along a displacement axis normal to the irradiation plane,
wherein said detector slit has at least one dimension, along the displacement axis,
a patient collimator located between said emission device and said patient space, said patient collimator comprising a X-ray absorbing plate in which a X-ray-transparent patient slit is formed, said patient slit having at least one dimension along the displacement axis, and defining said irradiation plane,
wherein the motoring device is also adapted to cause a relative movement of the patient collimator relative to the patient along the displacement axis, a control device adapted to cause the emission device and detection device to operate during said movement, so as to take a plurality of acquisitions, each taken along the same incidence direction, and each in a respective one of a plurality of different positions along said displacement axis, wherein the imaging apparatus comprises a setting device adapted to modify said dimension of said detector slit, wherein the control device comprises a computing device adapted to receive, as input, at least a parameter related to the patient, and to determine, based on said parameter and on a database, said dimension to be set by the setting device, a second emission device adapted to emit X-rays, in a second incidence direction, wherein the second irradiation plane is parallel to the irradiation plane, a second detection device adapted to detect X-rays, said second emission device and second detection device being located on either side of said patient space, a second detector collimator located between said patient space and said second detection device, said second detector collimator comprising a X-ray absorbing plate in which a X-ray transparent detector slit is formed, said detector slit having at least one dimension, along said displacement axis, wherein the motoring device is also adapted to cause a relative movement of the second emission device, the second detection device and the second detector collimator relative to the patient, along said displacement axis, wherein the control device is adapted to cause the second emission device and second detection device to operate during said movement, so as to take a plurality of second acquisitions each taken along the same second incidence direction, normal to said incidence direction, and each second acquisition being taken in a respective one of a plurality of different positions along said displacement axis, and wherein the setting device is adapted to modify said dimension of the slit of said second detector collimator and is adapted to modify said dimension of said slit of said second detector collimator independently from dimensions of slits of said patient and detector collimators.

2. Imaging apparatus according to claim 1, wherein the setting device is adapted to modify at least said dimension of the slit of said patient collimator.

3. Imaging apparatus according to claim 1, wherein at least one slit is rectangular, having a height measured along said displacement axis, and a width normal thereto, and wherein said setting device is adapted to modify the width of said slit.

4. Imaging apparatus according to claim 1, wherein the control device comprises a computing device adapted to receive, as input, at least a parameter related to at least one dimension of at least one slit, and to determine, based on said parameter, at least one dimension of another slit to be set by the setting device.

5. Imaging apparatus according to claim 1, wherein the setting device is adapted to modify a dimension of one slit during said relative movement.

6. An imaging apparatus according to claim 1, wherein said movements of the emission device and of the second emission device relative to the patient are synchronized, and wherein the control device is adapted to synchronize operation of said emission device and detection device with operation of said second emission device and second detection device.

* * * * *